US 6,632,204 B2

(12) United States Patent
Guldfeldt et al.

(10) Patent No.: US 6,632,204 B2
(45) Date of Patent: Oct. 14, 2003

(54) EXTERNAL URINARY CATHETER DEVICE FOR THE RELIEF OF MALE URINARY INCONTINENCE (75) Inventors: Signe Uhre Guldfeldt, Hillerod (DK); Henrik Lindenskov Nielsen, Smorum (DK); Allan Tanghoj, Kokkedal (DK)

(73) Assignee: Coloplast A/S, Humlebaek (DK)

( * ) Notice: Subject to any disclaimer, the term of this patent is extended or adjusted under 35 U.S.C. 154(b) by 222 days.

(21) Appl. No.: 09/756,288

(22) Filed: Jan. 9, 2001

(65) Prior Publication Data

US 2002/0087130 A1 Jul. 4, 2002

(30) Foreign Application Priority Data

Jan. 3, 2001 (DK) .................................. 2001 00008

(51) Int. Cl.⁷ ................................................ A61F 5/44
(52) U.S. Cl. ........................ 604/349; 604/544; 604/355
(58) Field of Search ................................ 604/327, 346, 604/347, 349, 350–352, 355, 540, 544

(56) References Cited

U.S. PATENT DOCUMENTS

| 3,598,124 A | * | 8/1971 | Andersen et al. ............ 604/544 |
| 3,742,953 A | * | 7/1973 | Lee .............................. 604/352 |
| 3,800,795 A | | 4/1974 | Walker ......................... 128/275 |
| 3,835,857 A | * | 9/1974 | Rogers et al. ................ 604/349 |
| 4,388,923 A | | 6/1983 | Heimreid ..................... 604/352 |
| 4,443,217 A | | 4/1984 | Izumi ........................... 604/73 |
| 4,656,675 A | | 4/1987 | Fajnsztajn .................... 4/144.4 |
| 4,713,067 A | * | 12/1987 | Rothenberg et al. ......... 604/353 |
| 5,002,541 A | * | 3/1991 | Conkling et al. ............ 604/319 |
| 5,211,640 A | | 5/1993 | Wendler ....................... 604/349 |
| 5,263,947 A | | 11/1993 | Kay ............................. 604/331 |
| 5,401,264 A | | 3/1995 | Leise, Jr. ..................... 604/333 |
| 5,554,141 A | | 9/1996 | Wendler ....................... 604/352 |
| 5,622,183 A | | 4/1997 | Hazard et al. ............... 128/761 |
| 5,685,870 A | * | 11/1997 | Tanghoj ....................... 604/349 |
| 5,741,240 A | * | 4/1998 | Olsen .......................... 604/353 |
| 5,779,964 A | | 7/1998 | Welch et al. ................. 264/255 |
| 5,827,247 A | | 10/1998 | Kay ............................. 604/327 |
| 5,897,540 A | | 4/1999 | Grundke et al. ............. 604/352 |
| 6,068,618 A | | 5/2000 | Anderson ..................... 604/349 |
| 6,132,407 A | * | 10/2000 | Genese et al. ............... 604/327 |
| 6,165,159 A | * | 12/2000 | Blanton ....................... 604/333 |

FOREIGN PATENT DOCUMENTS

| CA | 1 184 818 | 2/1985 |
| EP | 0 706 355 | 3/1997 |
| EP | 0 706 356 | 3/1997 |
| GB | 2 075 847 | 11/1981 |
| GB | 2 103 488 | 2/1983 |
| GB | 2 126 483 | 3/1984 |

* cited by examiner

Primary Examiner—Weilun Lo
Assistant Examiner—Michael G. Bogart
(74) Attorney, Agent, or Firm—Jacobson Holman PLLC

(57) ABSTRACT

An external urinary catheter for the relief of male urinary incontinence is provided. The catheter comprises a contact member which is adapted to be engaged with at least the extreme portion of a penis, said contact member being connected to a discharge conduit via an opening in the distal end section of the contact member. The catheter is provided with an aperture. A membrane, which is capable of selectively passing gases but retaining urine, is fastened to the surface surrounding the aperture. The membrane is at least partly protected by a shield. At least one vent for allowing gases to be in substantially unhindered contact with the external surface of the membrane is arranged in the catheter.

16 Claims, 3 Drawing Sheets

EXTERNAL URINARY CATHETER DEVICE FOR THE RELIEF OF MALE URINARY INCONTINENCE

INTRODUCTION

The present invention relates to an external urinary catheter device for the relief of male urinary incontinence, comprising a contact member which is adapted to be engaged with at least the extreme portion of a penis; an opening formed in a distal end section of the contact member and positioned substantially opposite the urethral orifice in the position of use, and a discharge conduit connected with the opening to provide a sealed urine flow passage extending in a substantial axial direction towards the exterior of the catheter device. The invention also pertains processes for manufacture of an external urinary catheter device for the relief of male urinary incontinence as well as uses of catheters of this kind.

BACKGROUND ART

For the relief of male urinary incontinence external catheters are generally used in the form of condom-like tubular sheaths to be placed externally on penis and having a discharge spout which via a hose is connected with a urine collection bag. Such external catheters are known in numerous designs and in many cases serve as a satisfactory solution of male incontinence problems. However, the complete envelopment of penis may give rise to trouble, partly because the application which is effected by unrolling the catheter requires a certain length of penis, partly in use due to the fact that the envelopment of the full length of penis with the catheter, which is generally fastened adhesively either by means of a separate adhesive strip or by means of an internal adhesive layer, involves strain of the skin of penis. Furthermore, the constant humid environment from the delivered urine may cause skin problems, such as allergy and maceration and even ulceration.

In recent years various suggestions have been presented in the prior art concerning the use in a urinary catheter of an inner member or a contact member, which in a position of use is positioned between the surface of the corona and the foreskin of the penis.

Thus, from GB-A-2 075 847 an device is known, which comprises a relatively short funnel-like uridom devise to be placed directly against the corona of the penis and to be kept in place under the foreskin. Around a discharge conduit of the device an external sheathing body is fastened in an inverted position to be brought into engagement with the external side of the foreskin after application of the uridom device to maintain the device in place by means of the sandwich position of the foreskin between the contact member and the external sheathing body.

Another design is disclosed in GB-A-2 126 483, wherein a more safe retainment of the device in the position of use is implemented by use of a tubular urine ducting device, e.g. of silicone rubber, arranged outside the corona in extension thereof, so that a rather severe extension of the foreskin is required to keep the tubular device in place by arrangement of an adhesive strip or strap member on the external side of the foreskin. Evidently, the rather severe extension of the foreskin required to keep the tubular device in place causes considerable discomfort in use.

In EP-B-0 706 355 and EP-B-0 706 356 external urinary catheters are disclosed in which a safe retainment in the position of use is obtained with considerably less discomfort to the user by means of a short inner contact member designed with improved form stability in its distal end part. Aiming at keeping the contact member safely in place under the foreskin the catheter is provided with a separate substantially bowl-shaped outer holder member displaceably surrounding a discharge conduit of the catheter device. The outer holder member is movable between an application position and a position of use.

Urinary catheters are generally connected via a hose to a urine collection bag. The wearer of the urinary catheter suitably places the urine collection bag in a position lower than the position of the urinary catheter to ensure that the urine effectively is drained off by gravity. To allow free movement of the wearer of the urinary catheter the urine collection bag is generally positioned at a part of the leg. Generally, it is preferred to position the urine collection bag at the shin to drain off urine in a standing as well as a sitting position. Furthermore, this position of the urine collection bag provides for the possibility of hiding it behind a trouser leg.

When using the prior art catheters mentioned above the problem arise, following a discharge of urine, that the unbroken column of urine in the hose give rise to a considerable built-up of sub-pressure at the surface of the corona. The wearer of the urinary catheter is subjected to discomfort, especially on extended exposure to the sub-pressure. Suction marks have been observed on the corona due the exposure to sub-pressure. In severe cases, oedema and subsequent infection has been developed.

It has been suggested to overcome this problem by incorporating a vent or a valve in the urine collection bag or the lower part of the hose allowing the surrounding air to communicate with the interior of the catheter-hose-bag environment. Reference is made to e.g. U.S. Pat. Nos. 3,800,857, 3,835,857, and 5,622,183. However, the position of a vent or valve in the bag or the lower part of the hose entails the potential risk that urine, when the bag is full or about to be full, will escape the urine collection bag.

Another suggestion is disclosed in U.S. Pat. No. 5,897,540 wherein a slit-shaped opening is provided in a condom-like device for drainage of uncontrolled urine release. The opening is provided for ventilation of the space entrapped between the device and the penis and is placed in the position of use at the main body of the penis well behind the corona. The opening is not provided with a filter or similar means. A further suggestion is disclosed in U.S. Pat. No. 4,656,675, which describes a condom-like device for draining off urine. The device is provided with a filter covering a hole positioned at a point close to the source of urine. The filter is capable of passing air but impervious to liquid at relative low pressures. A major drawback of this suggestion is that the filter is placed at an exposed position. The wearer of the device must be careful since the filter easily can be ripped off by abrasion or accident and the urine will tend to be conveyed through the hole in the device and not as intended through the hose.

It is the object of the present invention to avoid all or some of the above discussed problems and drawbacks of the prior art urinary catheters. Especially, it is an object of the present invention to provide a urinary catheter device having an enhanced reliability and durability due to reduced risk of deterioration.

DESCRIPTION OF THE INVENTION

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The external urinary catheter device of the kind disclosed in the introduction is, according one aspect of the invention, characterized in that an aperture is provided in a distal part of the contact member or in the discharge conduit; a membrane is fastened to the surface surrounding said aperture, the membrane being capable of selectively passing gases but retaining urine; a shield is at least partly protecting the membrane; and at least one vent is arranged for allowing gases to be in substantially unhindered contact with the external surface of the membrane.

The contact member and optionally also further components of the catheter device according to the invention, such as the discharge conduit and the shield, may be made from any material which is suitable for engagement with the sensitive skin of the corona and the foreskin. Suitable materials include thermoplastic elastomeric materials like styrene-butadiene-styrene (SBS), styrene-isoprene-styrene (SIS), styrene-ethylene/butadiene-styrene (SEBS), styrene-ethylene/propylene-styrene (SEPS), polyethers, polyesters, polyamides, polyurethane or any combination thereof; thermoplastic materials such as plasticized polyvinylchloride (PVC), and polyethylene; or curable elastomeric materials like nitril rubber, chloroprene rubber, natural rubber latex, silicone rubber, liquid silicone, polyisoprene or polyurethane. Preferred materials are SEBS and silicone rubber.

The membrane in the device according to the invention allows gas to pass, whereby it is ensured that the amount of urine discharged from a wearer may be drained to a urine collection bag via a hose without leaving a substantial amount of urine in the hose giving rise to a sub-pressure at the surface of the corona. The term gas as used in the current context means normally ambient air (a gas mixture of predominately nitrogen, oxygen, and water vapour), however, other gases or compositions of gases may come into play. Following a urine discharge the column of urine in the hose will gradually sink to an equilibrium level such that the pressure in the hose above the urine surface essentially corresponds to the pressure of the surrounding environment. A minor column of urine may be present due to a capillary effect and resistance in the membrane, however without entailing a substantial pressure effect on the surface of the corona.

The aperture provided in the distal part of the contact member or the discharge conduit may have any suitable dimension. The longest diagonal of the aperture may be larger than the diameter of the discharge conduit. However, to avoid a weakening of the discharge conduit, it is preferred that the aperture has a longest diameter less than the diameter of the discharge conduit. A suitable longest diagonal of the aperture is about 0,25 to 0,75 times the inner diameter of the discharge conduit. Preferably the circumference of the aperture is a circle, however other geometrical shapes might be suitable, such as ovals or polygons. Further suitable shapes are constituted by organic shapes. If desired, more than one aperture may be present in the device. The aperture is preferably positioned at a part of the discharge conduit close to the urethral orifice or the distal part of the contact member to obtain sufficient ventilation. Generally, it is to be avoided to arrange the aperture in a part of the discharge conduit intended to engage with a connector linking the device of the invention with a hose member, to prevent the risk of insufficient gas communication between the inner surface of the membrane and the interior of the discharge conduit. A preferred position of the aperture is in the proximal part of the discharge conduit close to the urethral orifice in a position of use.

A membrane is fastened to the surface surrounding the aperture, the membrane being capable of selectively passing gases but retaining urine. During discharge of urine from the urethral orifice the membrane effectively prevent urine from penetration and thus secure a sealed urine flow passage. Following the discharge of urine gas from the surrounding environment is penetrating the pores of the membrane and consequently, the column of urine in the hose is levelled. The membrane suitably maintain the desired selectivity at the relatively low pressures normally expected during use of the catheter device according to the invention. Normally, the water entry pressure of the membrane should be at least 100 mbar above ambient pressure.

The membrane is generally a thin, hydrofobic, porous sheet having the ability of allowing gas, i.e. air, to penetrate but not urine which is retained. A wide range of materials may be used for the membrane. Preferred materials are generally polymers with a low surface tension to water. Examples of suitable polymers are polyethylene, polypropylene, polyurethane, and polytetrafluorethylene (PTFE). Membranes of PTFE is commercially available under various trademarks, e.g. Goretex®. A preferred membrane of polyethylene is commercially available under the trademark Tyvek®.

While the membrane in one aspect of the invention is designed to retain urine at least at the relatively low pressures expected during normal use, it may be desirable, in another aspect of the invention, to use a embrane which at pressures above the level normally expected during use, is adapted to allow the passage of urine to avoid backing up of urine against the penis or ballooning of the foreskin. As an example, a sudden rise in pressure is obtained if the hose is kinked. In accordance with the second aspect of the invention the membrane is adapted allow the passage of urine at pressures over 80 mbar above ambient pressure, preferably over 100 mbar above ambient pressure.

The fastening of the membrane to the surface surrounding the aperture is normally conducted in order to secure a water-tight attachment of the membrane around the aperture. Any suitable method of fastening may be applied, including adhering, rivetting, partly dissolution by solvents, mechanical stress, or welding. Various suitable welding methods exist e.g. thermal, high frequency, ultrasonic, induction, or laser welding. In one aspect of the invention an adhesive is used for adhering the membrane to the surface surrounding the aperture since this method provides a simple and cost-effective way to obtain an effective attachment of the membrane to the surface surrounding the aperture. In another aspect of the invention a rivet is used to fasten the membrane to the surface surrounding the aperture, whereby the membrane is fixed between the male and the female parts of the rivet to providing an effective mechanical attachment of the membrane to the surface surrounding the aperture.

In still another aspect of the invention a fastening of the membrane to the surface of the aperture is obtained by melting the surface surrounding the aperture to an opposite surface of the membrane by welding or exposure to solvents. It is, in general, preferred to use welding, which includes applying an amount of heat sufficient to melt a part of the plastic material, allowing penetration of the melted plastic material into the pores of the membrane and subsequent allowing solidification of the plastic material. Thus, a simple and reliable way to attach the membrane to the surface around the aperture is obtained. A method especially suitably for attaching the membrane to the surface surrounding the aperture is ultrasonic or thermal welding.

In some embodiments of the invention it is advantageous to depress or sink an area surrounding the aperture and arrange the membrane in this depression. In such embodiments a space above the external surface of the membrane is generally obtained which allow sufficient ventilation of gases to and from the membrane surface.

In a preferred embodiment of the invention the contact member is integrally connected with the discharge conduit via the opening formed in the distal end section of the contact member. This embodiment makes it possible in a single component of the catheter device to integrate several functions, thus, increasing the industrial processability and securing a sealed urinary flow passage. In some areas of application, it may be useful to connect the discharge conduit to the opening formed in the distal end section of the contact member through a stretchable link to maintain the intimate engagement of the contact member with the penis in a position of use even under tensile load conditions acting on the discharge conduit. The stretchable link may for instance be a bellows-shaped member.

The contact member adapted to be engaged with a penis may be an inner member arrangeable in a position of use between the foreskin and the corona of the penis, an outer member adapted to be positioned on the external face of a penis to provide a sealed contact, and a combination thereof, i.e. an inner member as well as an outer holder member.

In case the contact member is an inner member arrangeable in a position of use between the foreskin and the corona of a penis it may comprise a shoulder-like ledge at a substantially plane abutment face of the inner member around and substantially perpendicular to the discharge conduit to retain the inner member in contact with the corona solely by means of the foreskin contacting the outer side of the contact member. An inner member of this kind is disclosed in EP 706 355 B1, the entire disclosure thereof being incorporated herein by reference.

Another suitable inner member which is arrangeable between the foreskin and the corona of the penis or solely on the corona of the penis, e.g., in the absence of foreskin in case of circumcising, comprises a plurality of leaves connected to a housing. The leaves are comprised of a film having an adhesive layer on their interior surface therof to secure an attachment of the device to the corona of the penis. Preferably, the film as well as the adhesive layer is vapour permeable to increase the comfort of the wearer. An inner member of this kind is disclosed in U.S. Pat. No. 5,263,947, the entire disclosure thereof being incorporated herein by reference.

For fastening the inner member in a position of use, it may be advantageous to provide the catheter device according to the invention with an outer holder member. The outer holder member is preferably formed in a distal end section with an opening for the discharge conduit and arrangeable in said position of use, in a substantially fixed axial position with respect to the discharge conduit for circumferential engagement with the external side of the foreskin.

The outer holder member may be made of any suitable soft elastic, semi-rigid or rigid material such as the plastic materials mentioned above for the contact member or, alternatively, it may be made in the form of a web of textile material like gauze, hydrocolloide skin adhesive covered with a film, or non-textile material. For improved engagement with the external side of the foreskin the inner engagement surface of the outer holder member may be coated with a layer of a skin-friendly adhesive, e.g. a hydrocolloide skin adhesive. Such an adhesive layer may be dimensioned with controlled adhesive properties and/or be applied in various patterns as known in the art to control the adhesive force. By use of an adhesive layer the length of the outer holder member in the position of use may be reduced to cover an even shorter part of the foreskin in order to increase comfort in connection with wear or removal of the catheter device.

The inner member may be permanently connected with a surrounding outer holder member having an opening for the discharge conduit by connection means. Suitably, said connection means is designed also to comprise the shield for the catheter according to the invention. Thus, the shield is preferably an extended part of the distal end section of the outer holder member. The connection means serving the dual purpose of permanently connecting the contact member with the outer holding member and shielding the membrane is in one aspect of the invention an essentially tubular member arranged around and having walls substantially parallel to the axis of the discharge conduit.

The contact member adapted to be in engagement with the penis, may in an aspect of the invention be adapted to be positioned on the external face of a penis to providing a sealed contact. To ensure an effective sealing between the contact member and the penis the contact member is suitably of a length covering the extreme portion, e.g. the foreskin or the corona, as well as the main body of the penis. An aperture can suitably be provided in a proximal part of the discharge conduit and covered with a membrane. A shield may be provided over the membrane as a separate or integral tubular member with an internal diameter substantially corresponding to or slightly smaller than the external diameter of the discharge conduit to fix the membrane. A stiffening member may be arranged inside the discharge conduit to provide a suitable abutment for the tubular member.

The urinary catheter of the invention comprises at least one vent which is arranged for allowing the gases, e.g. air, to be in substantially unhindered contact with the external surface of the membrane. The vent may be provided in any suitable way to ensure that the gases virtually unhindered can be conveyed from or to at least a part of the surface of the membrane. Thus, vents may be provided in the shield, the discharge conduit or both. Alternatively, the vent may be one or more hollow fibres or the like provided between the inner face of the shield and the outer surface of the discharge conduit to allow gas communication between the external face of the membrane and the surrounding environment.

In an aspect of the invention the vent is a single aperture provided in the shield. The aperture in the shield covers preferably the entire active membrane area to allow sufficient ventilation, however, especially in embodiments where the inner face of the shield is not in direct contact with the membrane, it may be desirable to provide the catheter according to the invention with an aperture smaller than the active membrane area to obtain a extended protection of the membrane.

In another aspect of the invention, the shield is provided with a plurality of apertures for ventilation. This aspect is of particular interest when a space above the external surface of the membrane is provide because the entire membrane area may be active. A space above the external membrane may be provided e.g. by fasting the membrane with a rivet or by attaching the membrane in a depression of the external surface of the discharge conduit. A plurality of relatively small apertures relative to a single larger aperture is regarded to be more effective for protecting the membrane since sharp or pointed devices to a larger extent is prevented from coming into intimate contact with the membrane from the outside of the catheter device.

A vent passage may also be provided using one or more tracks for channelling the gases to or from the external surface of the membrane to the surrounding environment. In particular, one or more track(s) may be provided in the inner face of the shield to establish a vent passage from the external surface of the membrane to the exterior of the catheter device.

In one aspect of the invention a plurality of tracks substantially parallel to the axis of the discharge conduit are formed in the inner face of the shield in a part or the entire circumference thereof establishing a vent passage from the external surface of the membrane to the exterior of the catheter device. The aspect of using tracks in the entire circumference of the inner surface of the shield could be advantageous from a production point of view as the assembling of the catheter is independent of the relative position of the shield and the membrane due to the rotational symmetry of the shield.

The depression (17) receiving the membrane may be provided with one or more depressed track(s) extending in a distal direction beyond the edge of the shield, said track(s) establishing a vent passage from the external surface of the membrane to the exterior of the catheter device. This alternative is attractive from a production point of view since the mould in which the device is formed, may be designed to provide an impression in the catheter part, said impression having the dual purpose of receiving the membrane and establishing an effective ventilation through the track(s). Moreover, the shield may have a tubular rotational symmetrical shape making it possible to assemble the catheter without observing the relative position of the shield and the membrane.

To obtain a large cross-section of the vent(s) one or more track(s) may be provided in the discharge conduit as well as the inner face of the shield, said tracks in common providing one or more channels for ventilation.

The track(s) provided in the discharge conduit and/or the inner face of the shield may have any suitable shape. Normally, the tracks are parallel to the axis of the discharge conduit to obtain the shortest channel. Other shapes may be considered to obtain specific properties of the catheter. As an example, the track may be provided with one or more bends to trap dust and to avoid penetration of pointed devices. As another example, tracks on the discharge conduit may be thread-like, whereby the gas is conducted around the axis of the discharge conduit.

The invention also pertain to a process for production of an external urinary catheter device for the relief of male urinary incontinence, which comprises the steps of providing a catheter part comprising a contact member which is adapted to be engaged with a penis; an opening formed in a distal end section of the contact member and positioned substantially opposite the urethral orifice in the position of use; and a discharge conduit connected with the opening to provide a sealed urine flow passage extending in a substantial axial direction towards the exterior of the catheter device, providing an aperture in a distal part of the contact member or in the discharge conduit, fastening a membrane to the surface surrounding said aperture, the membrane being capable of selectively passing gases but retaining urine, providing a shield to protect the membrane, and arranging at least one vent for allowing gases to be in substantially unhindered contact with the external surface of the membrane.

The catheter part comprising the contact member, opening and discharge conduit may be assembled of individual members or be produced in one piece. It is preferred to produce the catheter part in one piece due to the process economy by integrally connecting the contact member to the discharge conduit via the opening formed in the distal end section of the contact member. The catheter part may suitably be produced by plastic injection moulding using the polymer materials previously mentioned.

The aperture may be provided in any suitably way ensuring that gases substantially unhindered can communicate with the internal face of the membrane. In case the catheter part is produced in one piece by plastic injection moulding the mould is suitably adapted to provide the aperture during manufacture of the catheter part.

The membrane fastened to the surface surrounding the aperture is suitably fastened such that it is secured that a water-proof attachment is obtained. The fastening procedure may be any suitable method securing a water-proof attachment, including adhering, rivetting, partly dissolution by solvents, and welding. A preferred method of attachment comprise melting the surface surrounding the aperture to an opposite surface of the membrane. A preferred method of fastening the membrane to the surface surrounding the aperture is conducted by welding. Various welding methods are suitable, including ultrasonic, high frequency, induction, laser, and thermal welding. It is in general preferred to conduct the fastening by ultrasonic or thermal welding.

In an aspect of the invention according to the above process it pertains to the step of further providing the catheter part with an outer holder member for fastening the contact member in the position of use, wherein the outer holder member is formed in a distal end section with an opening for said discharge conduit and arrangeable in a position of use, in a substantially fixed axial position with respect to the discharge conduit for circumferential engagement with the external side of the foreskin.

The invention also provides a dip forming process for manufacture of an external urinary catheter device for the relief of male urinary incontinence, comprising the steps of a) providing a liquid polymer solution or emulsion comprising a polymer and a solvent or a diluent in an amount sufficient for permitting dip forming, b) providing a form having a first part for forming a contact member adapted to engage with a penis, a second part for forming an opening in the distal end section of the contact member and a third part for forming a discharge conduit, the first, second and third part being integrally connected, c) dipping said form in said solution or emulsion, d) removing the form from the solution or emulsion, e) allowing the solvent or the diluent to evaporate, and f) optionally, repeating the steps c), d), and e) until the device has attained the desired wall-thickness, wherein a membrane, capable of selectively passing gases but retaining urine, is arranged at the part of the form for forming the distal part of the contact member or the third part of the form forming the discharge conduit prior to dipping according to step c) or during evaporation according to step e).

During the manufacture it should be ensured that the polymer film resulting from step e) is prevented from coming into contact with the internal and the external face of the membrane or the polymer film is only releaseably attached to the membrane surface to allow the provision of an aperture and a vent on the internal and the external face of the membrane, respectively.

The liquid polymer solution or emulsion for performing the dip forming process according to the invention may comprise any polymer material which is suitable for engagement with the sensitive skin of the penis. Examples of suitable polymers include SBS, SIS, SEBS, natural rubber latex, SEPS, polyisoprene, polychloroprene, nitril rubber, silicone rubber, curable liquid silicone, polyurethane and any combination and quality thereof.

In the instance the liquid polymer is a solution, the solvent for dissolving the polymer is suitably an inert solvent of an aromatic or aliphatic nature or a combination thereof, however any solvent able to create a stable solution may be applied. The amount of solvent is appropriately sufficient for obtaining a solution without precipitations of polymer. In general the amount of solvent is higher than the minimum required for obtaining a solution to obtain a viscosity suitable for dip forming. A preferred amount of solvent is from 400 to 1200% by weight, based on the amount of polymer.

When the liquid polymer is an emulsion, the polymer is diluted with a suitable diluent. Preferably, the liquid polymer also contains an emulsifying agent to stabilize the emulsion. A suitable diluent is water. It is generally preferred that the emulsion contains sufficient diluent so as to obtain a viscosity of 100 cp to 1000 cp. The emulsion may optionally comprise a suitable coagulation agent, such as $Ca(NO_3)_2$ or $CaCl_2$, to obtain an increased wall-thickness. Furthermore, the emulsion may contain a curing agent. The curing agent may e.g. be activated by heat, moisture, ultra violet light, or electron beam. For certain kinds of polymers, e.g silicone, it is possible to prepare a liquid polymer suitable for dip forming without the usage of a diluent.

The form for dipping into the polymer solution or emulsion is appropriately adapted for receiving a membrane in the part of the form for forming the distal part of the contact member and/or in the third part of the form for forming the discharge conduit. The membrane may according to the invention be provided prior to dipping or during the evaporation.

In case the membrane is provided prior to dipping suitable means is provided for securing that the final device is not provided with a polymer film resulting from the evaporation step e). Various means exist, including providing the intended active membrane area with a coating which repels the liquid polymer, using a material for the membrane which in itself repels the polymer solution, covering the intended active membrane area with a removable item, and removing a releaseable attached polymer film from the membrane surface with suitable means.

A preferred method of avoiding a polymer film is to press a central part of the membrane against the form from the external side of the membrane by a suitable tool which covers the part of the membrane intended to be the active membrane area. While the central part of the membrane area is pressed against the form, edges and corners of the membrane sheet is embedded in the polymer matrix during the dip forming. It may be advantageous to provide the membrane on a suitable carrier, wherein the carrier material surrounds the active membrane area and is adapted to be able to anchor the membrane in the polymer matrix. Thus, the membrane is shielded as the edges and corners is embedded in the polymer matrix, whereby the risk of deteriorating the membrane during use is reduced. Furthermore, a vent passage is provided by the pressing tool.

It may be preferred to attach the membrane prior the dipping according to step c) to a raised platform to increase the anchoring effect of the material surrounding the active membrane area and to provide for an aperture having a less tendency to be occluded by the polymer solution during dipping. Preferably, the membrane is kept on the platform during the dip forming procedure by a suitable pressing means, which may allow for the production of a vent passage.

The membrane may also be provided prior to or during evaporation according to step e) or curing if a curing agent is provided in the polymer liquid. Suitably, a sufficient amount of solvent is allowed to evaporate to essentially preserve the dimension stability of an aperture being provided in the polymer film. A membrane sheet comprising an area intended to be active in the final device is arranged such that is covers the aperture and the area of the membrane surrounding the area intended to be active is attached the area surrounding the aperture. The attachment can be effected in any appropriate way, e.g. by pressing the surrounding area of the membrane into the still fluid polymer matrix or adhering the surrounding area of the membrane to the area surrounding the aperture by any suitable means following evaporation of an essential amount of the solvent. A shield may be provided aiming at protecting the membrane by a repetition of the steps c), d) and e). It must be secured during the repetition that at least one vent is arranged for allowing gases to be in substantially unhindered contact with the external surface of the membrane. The means for providing the vent can be similar to the means for avoiding the polymer film resulting from the evaporation step e), as discussed above. A preferred method is to press a tool against a central part of the external surface of the membrane to protect the intended active membrane area against coming into contact with the polymer solution.

The invention also pertains to a process for manufacture of an external urinary catheter device for the relief of male urinary incontinence, comprising the steps of providing a mould comprising a matrix and a core for plastic injection moulding, wherein the cavity defined by the matrix and the core comprises a first part for forming a contact member adapted to engage with a penis, a second part for forming an opening in the distal end section of the contact member and a third part for forming a discharge conduit, the first, second and third part being integrally connected, injecting a liquid plastic material into the cavity of the mould, solidification of the liquid plastic material, and recovering-the moulded device from the mould, wherein a membrane capable of selectively passing gases but retaining urine is arranged at the part of the cavity for forming the distal part of the contact member or the third part of the cavity for forming the discharge conduit.

The liquid plastic material for the injection moulding process is typically a melted thermoplastic material, which is solid at normal ambient temperatures or a curable liquid polymeric material such as liquid silicone.

During the injection moulding procedure according to the above process it should be ensured that neither the internal face nor the external face of the membrane is occluded by plastic material. In an aspect of the process of the invention the internal face of the membrane is covering an aperture and/or the external face of the membrane is protected with a shield having a vent.

A vent allowing gases to communicate with the external face of the membrane may be provided by pressing a central part of the membrane against the core by a suitable tool from the matrix side. In addition or alternatively, an aperture allowing urine and gas to communicate with the interior of the membrane surface may be provided by pressing a central part of the membrane against the matrix with a suitable tool from the core side. Suitably, the part of the pressing tool which faces the membrane has an area which may cover a part of the membrane intended to be the active membrane area in the final device. The part of the membrane not pressed with the tool is embedded in the polymer matrix during the plastic injection moulding and provides for an attachment of the membrane to the polymer matrix. To ensure a proper attachment, the membrane may be provided on a carrier having properties which effectively anchor the membrane to the polymer matrix.

In may be advantageous to design the mould with a core and/or a matrix which comprise a raised platform as the tool for pressing the membrane against the matrix and/or the core. The embodiment in which the core as well as the matrix comprise a raised platform, the membrane is arranged within the cavity by pressing the two raised platforms against the membrane. This embodiment ensures the production of a device wherein an aperture as well as a vent is provided. Furthermore, the membrane is shielded from deterioration due to the embedment of the edges and corners of the membrane sheet.

DETAILED DESCRIPTION OF THE INVENTION

Figure 1:
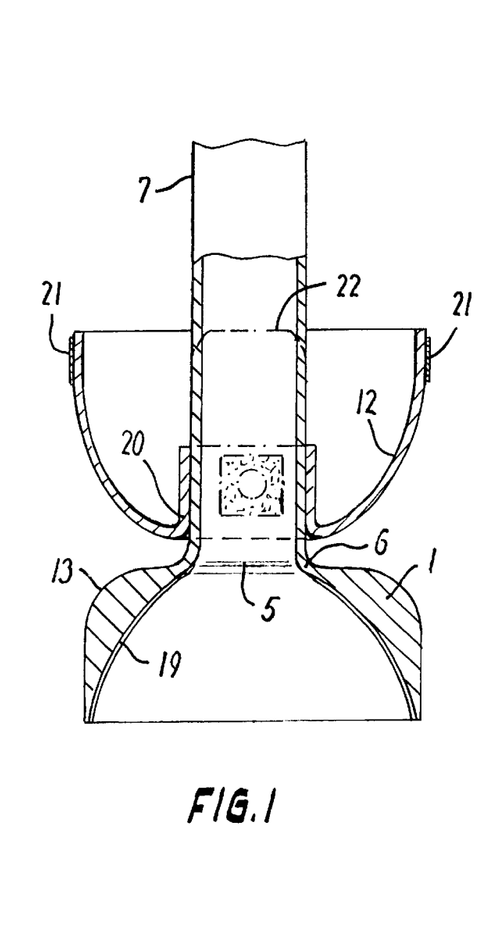
FIG. 1 shows a sectional view of an embodiment of the invention with an outer holder member in an application position.
Figures 2, 3:
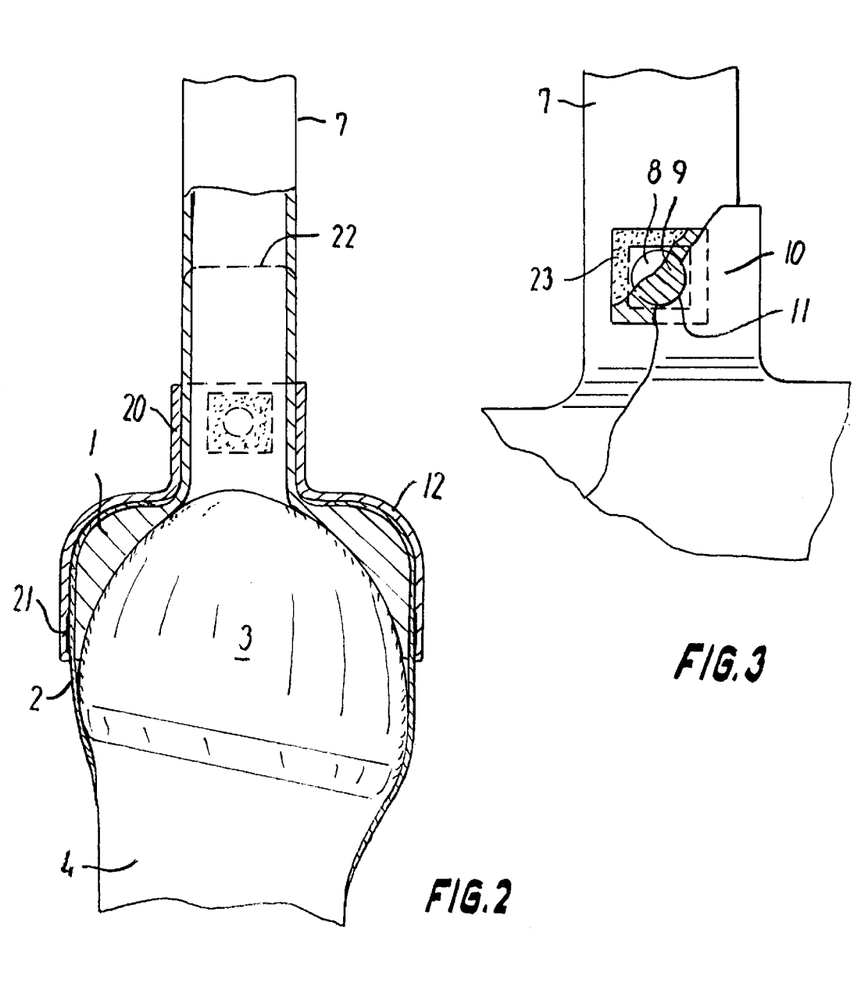
FIG. 2 shows a sectional view of the embodiment depicted in FIG. 1 with the outer holder member in a position of use.
FIG. 3 shows an enlarged view of the embodiment disclosed in FIGS. 1 and 2 with the layers in the vicinity of the membrane partly broken away.

The catheter device shown in FIGS. 1, 2, and 3 comprises a contact member 1 which is formed with an opening 5 which in a position of use as shown in FIG. 2 is situated opposite the urethral orifice in the corona 3 of a penis 4. At the opening 5, the distal end section 6 joints discharge conduit 7 by which the catheter may be connected e.g. with a hose member, through which discharges of urine may flow from the contact member into a collection bag not illustrated. Thereby a sealed urine flow passage is provided to extend, from the inner side of the contact member 1 facing the urethral orifice, in a substantially axial direction towards the exterior of the catheter device.

As shown in FIG. 2 the contact member 1 is formed to be placed in use under the foreskin 2 of the penis 4 in contact with the corona 3.

In the distal end section 6 around the discharge conduit 7 the contact member 1 is designed with increased form stability so as to form a shoulder-like ledge 13 having e.g. a substantially flat end face so that in use the contact member 1 is retained by the foreskin 2.

To provide an improved sealing effect against the corona 3 the inner side of the contact member 1 is coated with a layer 19 of a skin-friendly adhesive as used for medical devices intended to be in contact with sensitive skin tissue.

In the embodiment shown, the discharge conduit 7 and the contact member 1 are connected with a surrounding outer holder member 12 having an opening for the discharge conduit 7 via the tubular connection ember 20. As shown in FIGS. 1 and 2, the outer holder member 12 is formed as an invertible substantially bowl-shaped member, which from the inverted application position in FIG. 1 can be brought into the position of use by tilting it around the transition to the connection member 20. An annular applicator not shown on the figures for engagement with the extreme portions of the outer holder member 12 may be used to invert the outer holder member 12 from an application position depicted in FIG. 1 to a position of use depicted in FIG. 2. Such an annular applicator will be effective to facilitate accurate positioning of the contact member 1 relative to the corona during application of the catheter device.

The inner engagement surface of the outer holder member 12 is partly or totally coated with a layer 21 of a skin-friendly adhesive for improved engagement with the external surface of the foreskin 2. The provision of the adhesive is not compulsory, however, and may be dispensed with, since a sufficient holding force may be obtained by other means, e.g. dimensioning of the outer holder member with a length so as to cover, in the position of use, the entire external side of the foreskin surrounding the corona.

In order to facilitate removal of the catheter device after use the distal end of the tubular connection member 20 is formed with a projecting flap 22, which may serve as a grip which can be operated to remove the outer holder member 12 by pulling back the projecting flap 22 in a direction towards the inverted position, from which the holder member was originally applicated.

As shown in detail on FIG. 3 an aperture 8 is provided in a proximal part of the discharge conduit 7 relatively close to the urethral orifice in a position of use. A membrane 9 capable of selectively passing gases but retaining urine, is covering the aperture 8 and attached to the area of the discharge conduit surrounding the aperture 8 via an adhesive 23. The membrane 9 is in turn covered with a shield 10, which is a part of the tubular connection member 20, for providing protection of the membrane. A single vent 11 is provided in the shield 10 for allowing gases to be in substantially unhindered contact with the external surface of the membrane. The vent 11 in the shield 10 has a dimension corresponding to the dimension of the aperture 8 allowing the active membrane area virtually unhindered to communicate with the surrounding environment, while preventing the edges and corners of the membrane to be exposed to mechanical wear, thus reducing the risk of deterioration of the membrane.

Figure 4:
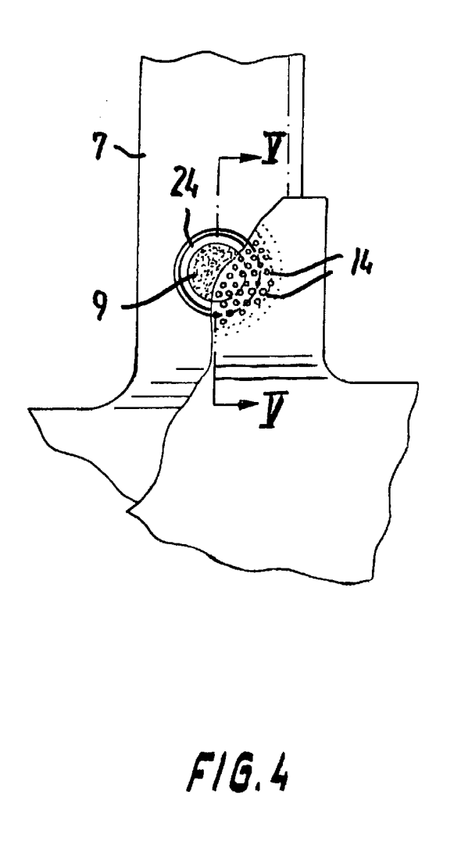
FIG. 4 shows a detail of a second embodiment of the invention with the shield partly broken away.
Figure 5:
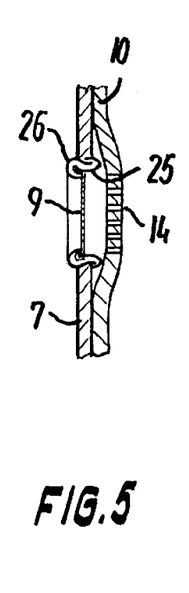
FIG. 5 shows a sectional view of the detail of the second embodiment on FIG. 4. The section is indicated by V on FIG. 4.

FIGS. 4 and 5 show an embodiment of the invention using a rivet 24 to fasten the membrane to an area of the discharge conduit surrounding the aperture. The membrane is fastened to the orifice of the rivet by clamping between the male 25 and the female 26 part of the rivet 24. The male part 25 of the rivet 24 shown on FIG. 5 provides a raised platform for the shield 10, whereby an increased space between the external side of the membrane and the shield is formed. The shield is provided with a plurality of apertures 14 as vents allowing a virtually unimpeded diffusion of gases between the space above the membrane surface and the surrounding environment.

Figures 6, 8:
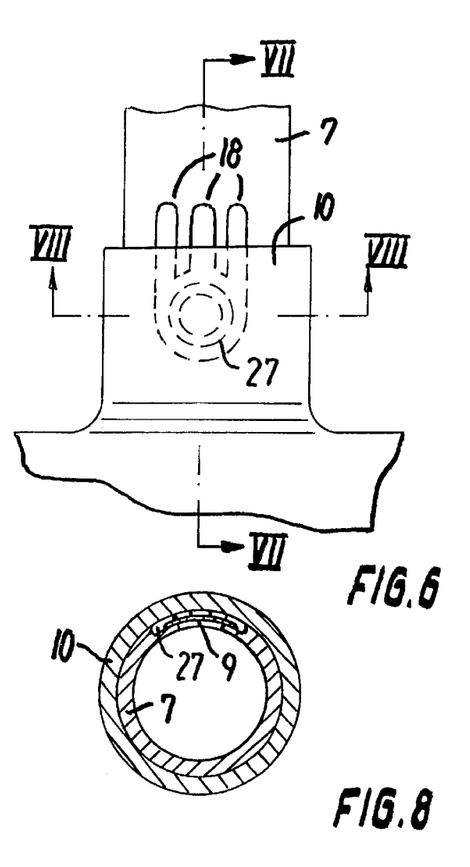
FIG. 6 shows a front view of a detail of a third embodiment of the invention.
FIG. 8 shows a sectional view of a detail of the embodiment shown on FIGS. 6 and 7. The section is indicated by VIII on FIG. 6.
Figure 7:
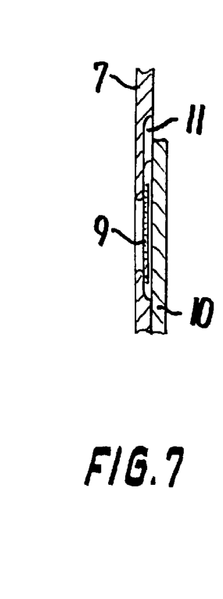
FIG. 7 shows a sectional view of the detail of the embodiment of FIG. 6. The section is indicated by VII on FIG. 6.

FIGS. 6, 7, and 8 show an embodiment of the invention where the membrane is depressed in the surface of the discharge conduit 7 and tracks 18 are provided for ventilation. A hand-like depression is cast in the outer face of the discharge conduit, said depression comprising a carpus 27 and three fingers 18 extending in a distal direction. The carpus 27 of the hand-like depression is provided with a membrane 9 attached to the area around the aperture by welding. A tubular shield 10 is covering the carpus 27 and a part of the fingers 18 but not the fingertips. During use of the catheter device of the invention air may be vented through the openings at the fingertips and conducted via the fingers covered by the shield 10 to the external surface of the membrane 9.

Figures 9, 11:
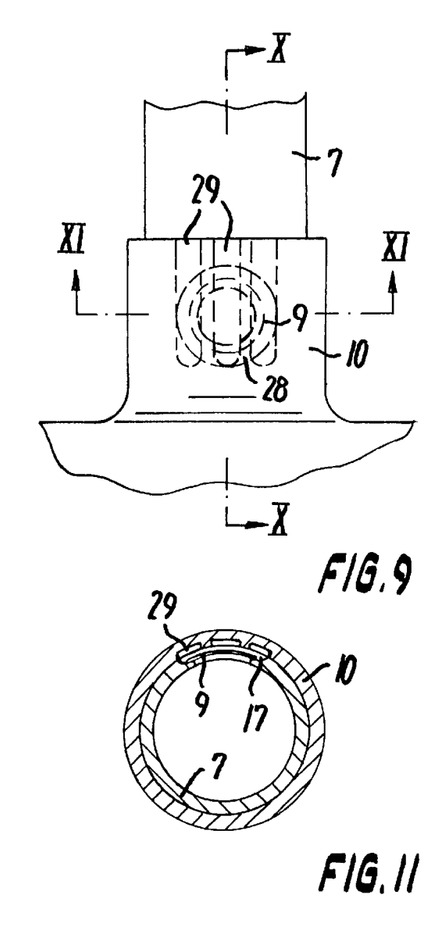
FIG. 9 shows a front view of a detail of a fourth embodiment of the invention.
FIG. 11 shows a sectional view of a detail of the embodiment shown on FIGS. 9 and 10. The section is prepared as indicated by XI on FIG. 9.
Figure 10:
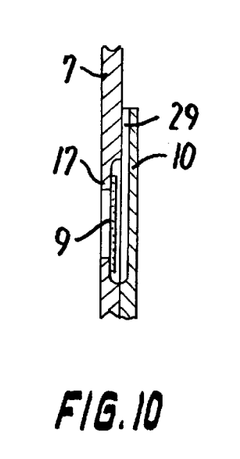
FIG. 10 shows a sectional view of a detail of the embodiment indicated on FIG. 9. The section is shown by X on FIG. 9.

FIGS. 9, 10, and 11 disclose an embodiment of the invention where the membrane is depressed in the surface of the discharge conduit and tracks in the inner face of the shield provides for the ventilation. A circular depression 28 is formed in the discharge conduit 7 in an area around the circular aperture 8. A membrane 9 is attached to the depressed area around the aperture by welding. A tubular shield 10 is covering the depression and extents over the circumference thereof. Three tracks 29 are provided in the inner face of the shield 10 to establish a vent passage from the external surface of the membrane to the exterior of the catheter device. In operation, air is sucked in at the opening formed by the tracks 29 in the edge of the shield 10. The air is subsequently conducted through the tracks to the external surface of the membrane.

Figure 12:
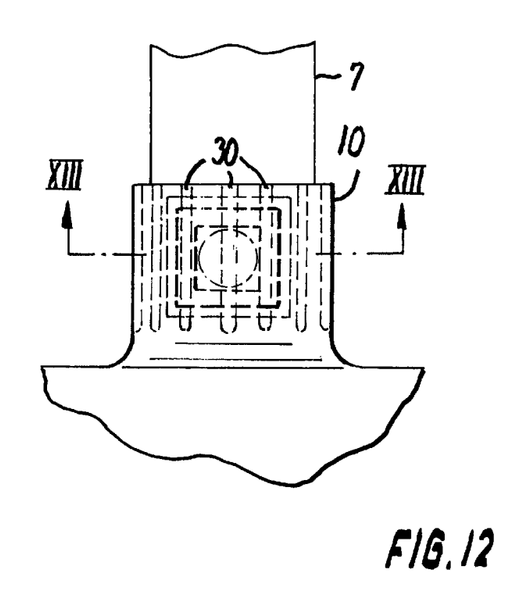
FIG. 12 shows a detail of a front view of a fifth embodiment of the invention.
Figure 13:
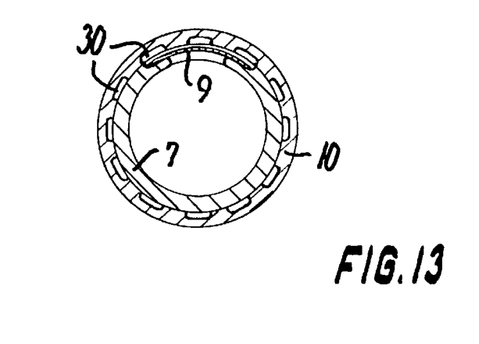
FIG. 13 shows a sectional view of a detail of the embodiment shown on FIG. 12. The section is indicated on FIG. 12 at XIII.

FIGS. 12 and 13 show an embodiment of the invention, in which the vent passage is provided by a plurality of tracks formed in the inner face of the shield. The membrane 9 is provided and covers the aperture as explained for the embodiment according to FIGS. 1, 2, and 3. A tubular shield 10 is surrounding the part of the discharge conduit harbouring the aperture covered with the membrane. The edge of the tubular shield extent above the upper edge of the membrane. A plurality of tracks 30 substantially parallel to the axis of the discharge conduit are formed in the inner face of the shield in the entire circumference thereof. In operation, air is sucked in at the openings formed by the tracks 30 in the edge of the shield 10 and subsequently conveyed to the external surface of the membrane. Thus, the tracks 30 establishes a vent passage allowing air from the exterior of the catheter to come into contact with the surface of the membrane.

While in the foregoing, embodiments of the invention have been disclosed in considerable detail for purpose of illustration, it will be understood by those skilled in the art that many of these details may be varied without departing from the spirit and scope of the invention.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An external urinary catheter device for the relief of male urinary incontinence, comprising:
    a contact member which is adapted to be engaged with at least the extreme portion of a penis;
    an opening formed in a distal end section of the contact member and positioned substantially opposite the urethral orifice in the position of use;
    a discharge conduit connected with the opening to provide a sealed urine flow passage extending in a substantial axial direction towards the exterior of the catheter device;
    an aperture provided in a distal part of the contact member or in the discharge conduit;
    a membrane fastened to the surface surrounding said aperture, the membrane being capable of selectively passing gases but retaining urine;
    a shield at least partly protecting the membrane; and
    at least one vent arranged in a portion of said shield overlying said membrane for allowing gases to be in substantially unhindered contact with the external surface of the membrane.

2. The external urinary catheter device according to claim 1, wherein the contact member is integrally connected with discharge conduit via the opening formed in the distal end section of the contact member.

3. The external urinary catheter device according to claim 1, wherein the contact member is an inner member arrangeable, in a position of use, between the foreskin and the corona of a penis.

4. The external urinary catheter device according to claim 3, wherein the inner member comprises a shoulder-like ledge at a substantially plane abutment face of the contact member around and substantially perpendicular to the discharge conduit.

5. The external urinary catheter device according to claim 1, further comprising an outer holder member for fastening the contact member in the position of use, wherein the outer holder member is formed in a distal end section with an opening for said discharge conduit and arrangeable in said position of use, in a substantially fixed axial position with respect to the discharge conduit for circumferential engagement with the external side of the foreskin.

6. The external urinary catheter device according to claim 1, in further combination with:
    a bag for collection of urine discharged from the catheter device; and
    a hose member connecting the catheter device and the bag.

7. The external urinary catheter device according to claim 1, wherein the vent is embodied as a plurality of apertures in said portion of the shield overlying said membrane.

8. The external urinary catheter device according to claim 1, wherein the membrane is fastened to the surface surrounding the aperture with an element that provides a raised platform for the shield, forming an increased space between the shield and an external side of the membrane.

9. A process for production of an external urinary catheter device for the relief of male urinary incontinence, which comprises the steps of:

providing a catheter part including a contact member which is adapted to be engaged with a penis, an opening formed in a distal end section of the contact member and positioned substantially opposite the urethral orifice in the position of use, and a discharge conduit connected with the opening to provide a sealed urine flow passage extending in a substantial axial direction towards the exterior of the catheter device;

providing an aperture in a distal part of the contact member or in the discharge conduit;

fastening a membrane to the surface surrounding said aperture, the membrane being capable of selectively passing gases but retaining urine;

providing a shield to protect the membrane; and arranging at least one vent in a surface of said shield overlying said membrane for allowing gases to be in substantially unhindered contact with the external surface of the membrane.

10. The process according to claim 9, wherein the contact member is integrally connected to the discharge conduit via the opening formed in the distal end section of the contact member.

11. The process according to claim 9 further comprising the step of providing the catheter part with an outer holder member for fastening the contact member in the position of use, wherein the outer holder member is formed in a distal end section with an opening for said discharge conduit and arrangeable in a position of use, in a substantially fixed axial position with respect to the discharge conduit for circumferential engagement with the external side of the foreskin.

12. An external urinary catheter device for the relief of male urinary incontinence, comprising:

a contact member which is adapted to be engaged with at least the extreme portion of a penis;

an opening formed in a distal end section of the contact member and positioned substantially opposite the urethral orifice in the position of use;

a discharge conduit connected with the opening to provide a sealed urine flow passage extending in a substantial axial direction towards the exterior of the catheter device;

an aperture provided in a distal part of the contact member or in the discharge conduit;

a membrane fastened to the surface surrounding said aperture, the membrane being capable of selectively passing gases but retaining urine;

a shield at least partly protecting the membrane; and at least one vent including at least one track arranged for allowing gases to be in substantially unhindered contact with the external surface of the membrane.

13. The external urinary catheter device according to claim 12, wherein the membrane is depressed in the discharge conduit and said track extends from the membrane to a point beyond the shield.

14. The external urinary catheter device according to claim 12, wherein the shield is tubular and said membrane is depressed in the discharge conduit, said vent including a plurality of tracks in an edge of the shield.

15. The external urinary catheter device according to claim 12, wherein the shield is tubular and surrounds at least part of the discharge conduit, said vent including a plurality of tracks formed in an inner face of said shield.

16. The external urinary catheter device according to claim 15, wherein said plurality of tracks are substantially parallel with a longitudinal axis of said discharge conduit.

* * * * *